US010416057B2

(12) United States Patent
Mohseni

(10) Patent No.: US 10,416,057 B2
(45) Date of Patent: Sep. 17, 2019

(54) UNIFIED PERFORMANCE TEST FOR VISCOELASTIC MATERIALS

(71) Applicant: Alaeddin Mohseni, Bethesda, MD (US)

(72) Inventor: Alaeddin Mohseni, Bethesda, MD (US)

(*) Notice: Subject to any disclaimer, the term of this patent is extended or adjusted under 35 U.S.C. 154(b) by 0 days.

(21) Appl. No.: 15/568,303

(22) PCT Filed: Mar. 17, 2017

(86) PCT No.: PCT/US2017/023000
§ 371 (c)(1),
(2) Date: Oct. 20, 2017

(87) PCT Pub. No.: WO2017/161292
PCT Pub. Date: Sep. 21, 2017

(65) Prior Publication Data
US 2018/0372606 A1 Dec. 27, 2018

Related U.S. Application Data

(60) Provisional application No. 62/309,932, filed on Mar. 17, 2016.

(51) Int. Cl.
G01N 11/00 (2006.01)
G01N 11/14 (2006.01)
(Continued)

(52) U.S. Cl.
CPC ............ G01N 11/142 (2013.01); C10C 3/002 (2013.01); C10C 3/18 (2013.01); G01N 11/165 (2013.01);
(Continued)

(58) Field of Classification Search
CPC ............... G01N 11/142; G01N 11/165; G01N 2011/145; G01N 33/42; G01N 2203/0094
See application file for complete search history.

(56) References Cited

U.S. PATENT DOCUMENTS

2005/0178209 A1* 8/2005 Kim .................... G01N 3/60
73/803
2010/0191110 A1* 7/2010 Insana .................. A61B 8/0825
600/438

(Continued)

OTHER PUBLICATIONS

Artcile titled "MSCR Implemenatation and Impacts on Asphalt Binder Grading" by Hanz et al. published on Feb. 19, 2015.*

Primary Examiner — Blake A Tankersley

(57) ABSTRACT

The use of recycled materials can have significant economic value. With the increasing quantity of recycled material used in viscoelastic materials, especially asphalt mixture, understanding how they interact with original materials to produce a mixture that performs successfully, becomes critical. Currently, the technology to determine the effect of additives on the performance of asphalt mixture is lacking. The present invention relates to a new unified methodology for mechanical testing of asphalt mixture and other viscoelastic materials that improves the current practice in speed, convenience, and accuracy. A new improved specimen mounting method on Dynamic Shear Rheometer (DSR), a new recovery method for fine portion of asphalt mixture, and three new tests for the performance of recovered material using DSR is disclosed. The new methods provide performance grading of asphalt mixtures that is new to the industry and provide necessary tools for determining the effect of recycled materials on performance.

17 Claims, 27 Drawing Sheets

Load and deformation for a Pulse Load Cycle Comprising Pulse Load and Zero Load

(51) Int. Cl.
*G01N 33/42* (2006.01)
*C10C 3/00* (2006.01)
*C10C 3/18* (2006.01)
*G01N 11/16* (2006.01)
*G01N 33/38* (2006.01)

(52) U.S. Cl.
CPC ............ *G01N 33/42* (2013.01); *G01N 33/38* (2013.01); *G01N 2203/0094* (2013.01)

(56) References Cited

U.S. PATENT DOCUMENTS

| | | | |
|---|---|---|---|
| 2011/0196073 A1* | 8/2011 | Fee | C08L 95/00 524/68 |
| 2013/0104776 A1* | 5/2013 | Vaidya | C08L 95/00 106/660 |
| 2013/0174666 A1* | 7/2013 | Hadj Henni | G01N 11/16 73/800 |
| 2013/0336720 A1* | 12/2013 | Jack | C08L 95/00 404/75 |
| 2015/0346182 A1* | 12/2015 | Mallela | G01N 33/383 73/803 |
| 2016/0130474 A1* | 5/2016 | Dongre | C09D 195/005 428/407 |

* cited by examiner

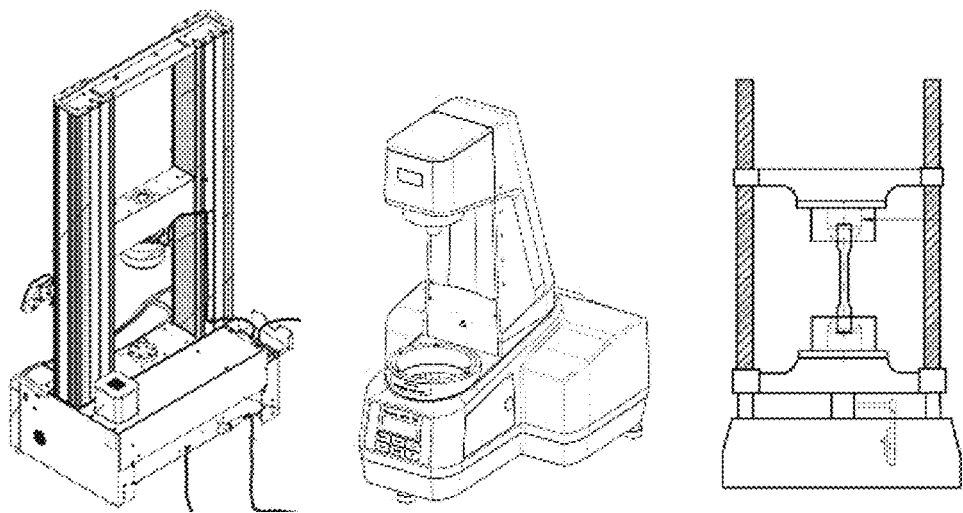
Fig. 1. (Prior Art) Test Loading Devices: Universal Testing Machine -UTM (Left) – Dynamic Shear Rheometer - DSR (middle) – Dynamic Mechanical Analyzer - DMA (right)

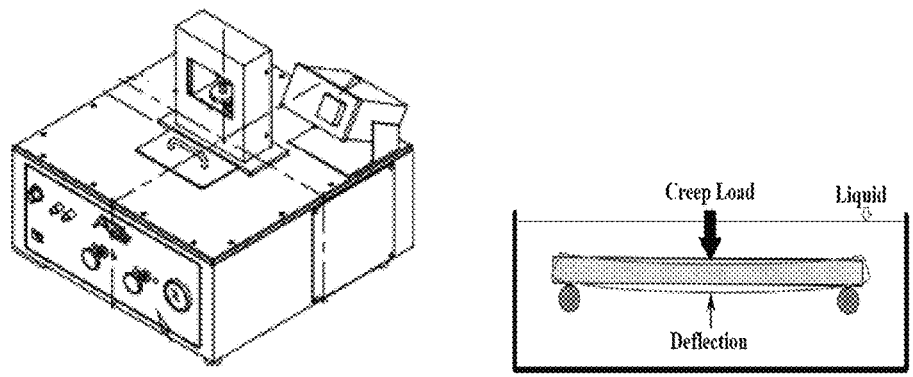
Fig. 2- (Prior Art) Bending Beam Rheometer -BBR Device (left) and Schematic of the BBR Test Three point Bending of Asphalt Bar in Chilled Fluid (right)

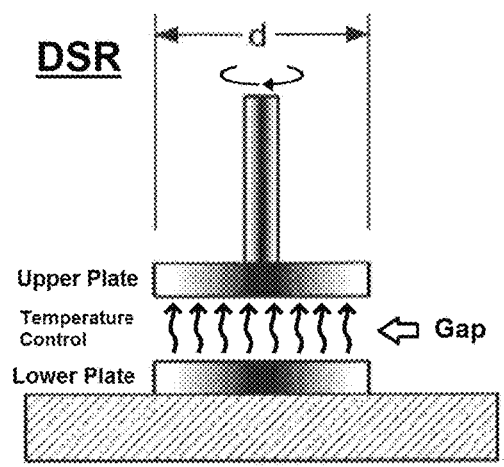
*Fig. 3- (Prior Art) Elements of a Parallel Plates DSR Consisting Two Plates that Create an adjustable Gap, Torque in one Plate, and Temperature Control for the Specimen*

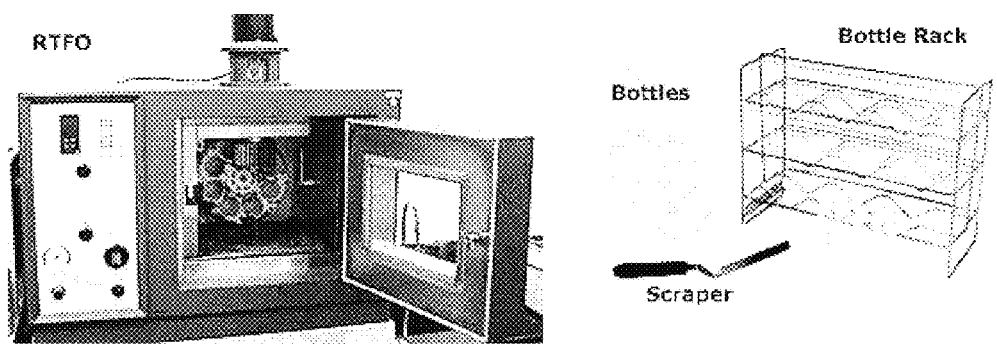
Fig. 4- (Prior Art) Rolling Thin-Film Oven (RTFO) Equipment (left) and Bottles (right)

Fig. 5- (Prior Art) Pressure Aging Vessel (PAV) used for long-term aging of asphalt binder

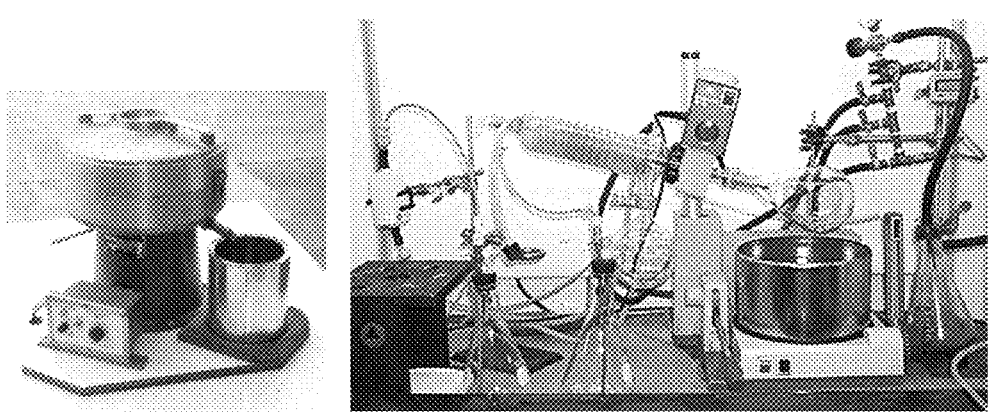
Fig. 6 – (Prior Art) Open Centrifuge Used for Solvent Extraction of asphalt mixture (left), Asphalt binder recovery using a Rotavapor recovery procedure (right)

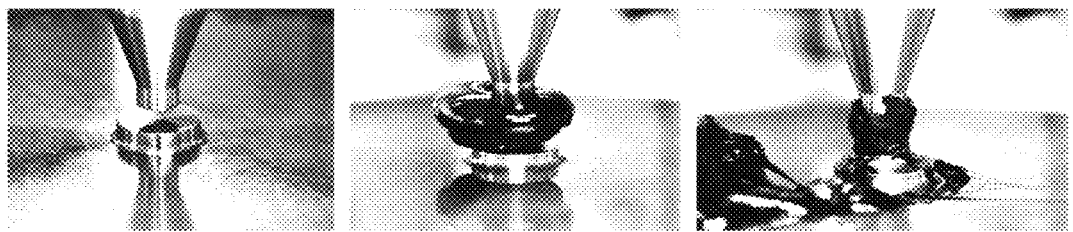
Fig. 7- (Prior Art) DSR Asphalt Mounting Method using Manual Trimming per ASASHTO 315

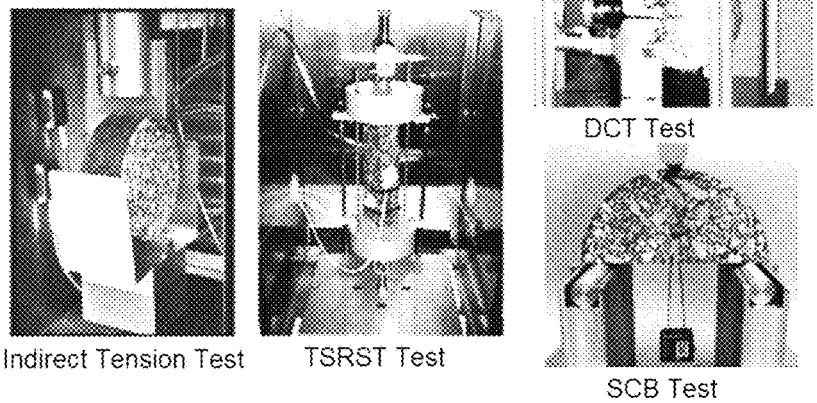
Fig. 8- (Prior Art) Various Low-Temperature Asphalt Mixture Testing Equipment

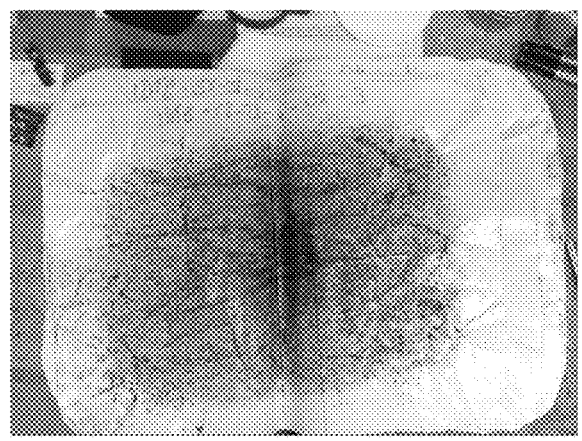
Fig. 9 –Silicon Paper with Asphalt Mixture Residue According to the Present Invention

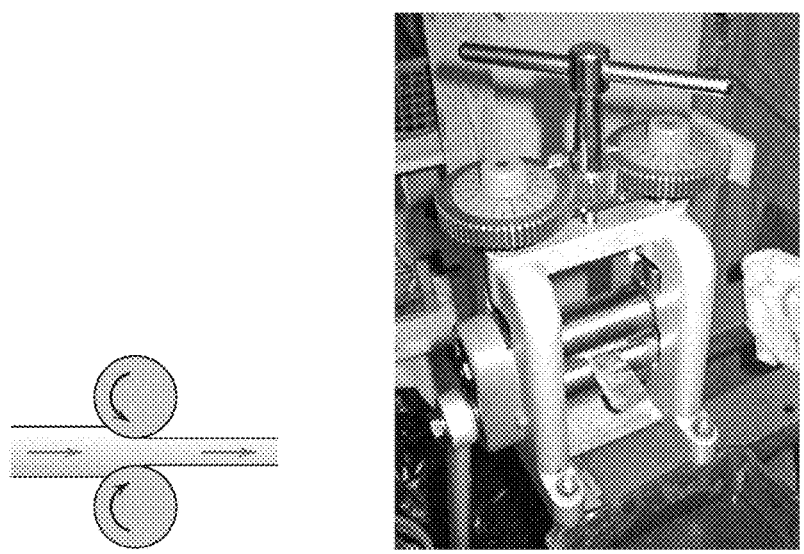
Fig. 10- Roller for maximum particle size detection of AMR (left) AMR wrapped in paper passed through rolling mill with gap set to maximum particle size plus paper thickness

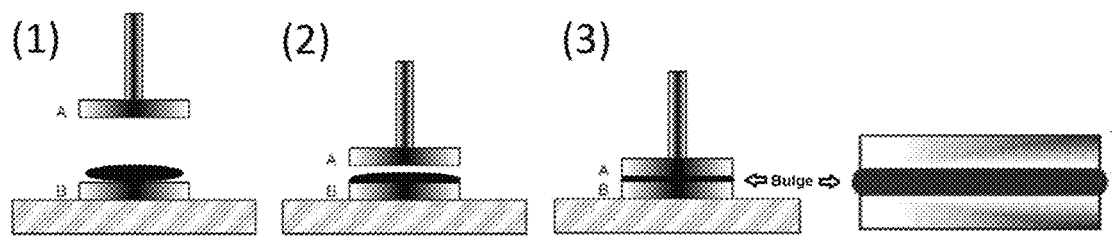
Fig. 11- Process of Mounting Asphalt Binder or AMR on DSR According to the Invention

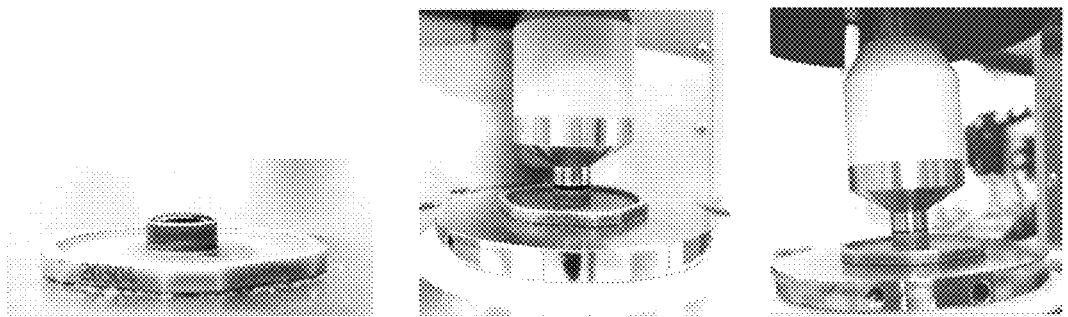
*Fig. 12- Melted Asphalt Binder on the DSR first plate (left), Mounted AMR with 1.0mm Gap (middle), and mounted asphalt Binder with 0.5-mm Gap (right)*

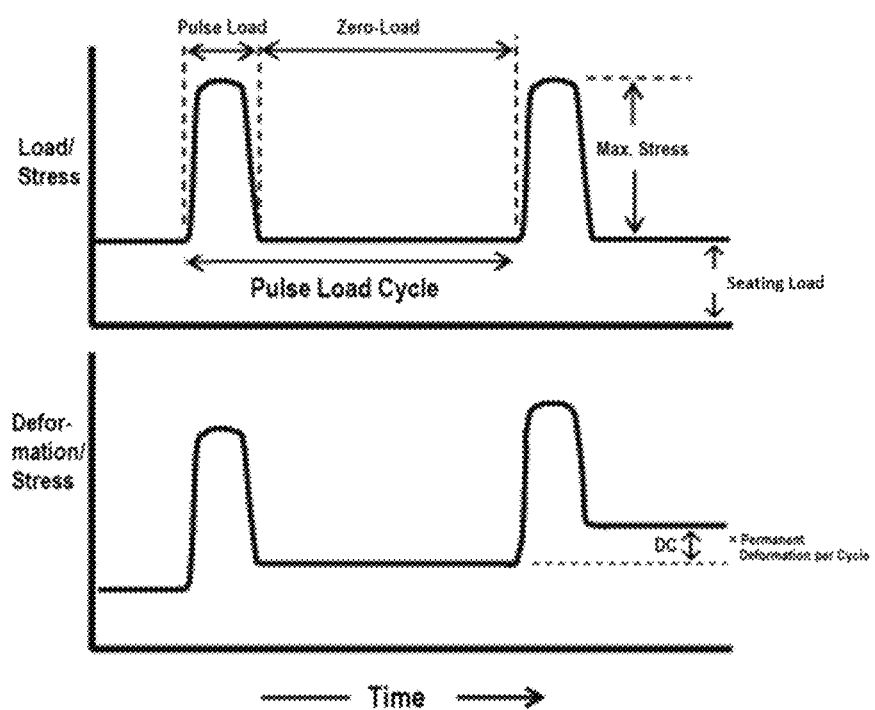
Fig. 13- Load and deformation for a Pulse Load Cycle Comprising Pulse Load and Zero Load

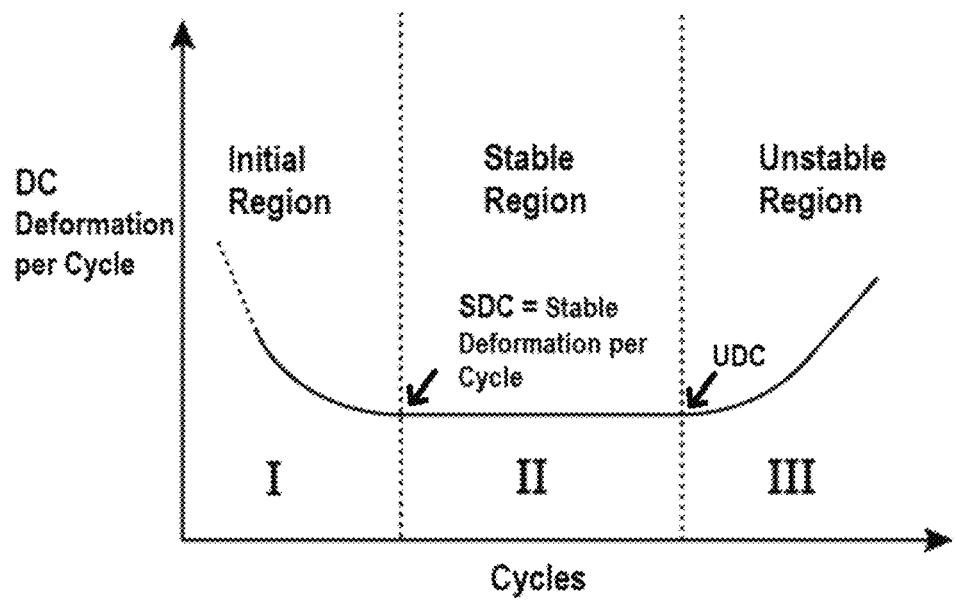
*Fig. 14- Loading Series (LS): the response (deformation) of VEM to a Series of loading cycles as applied to both Pulse Load Cycle (PLC) and Constant Load Cycle (CLC)*

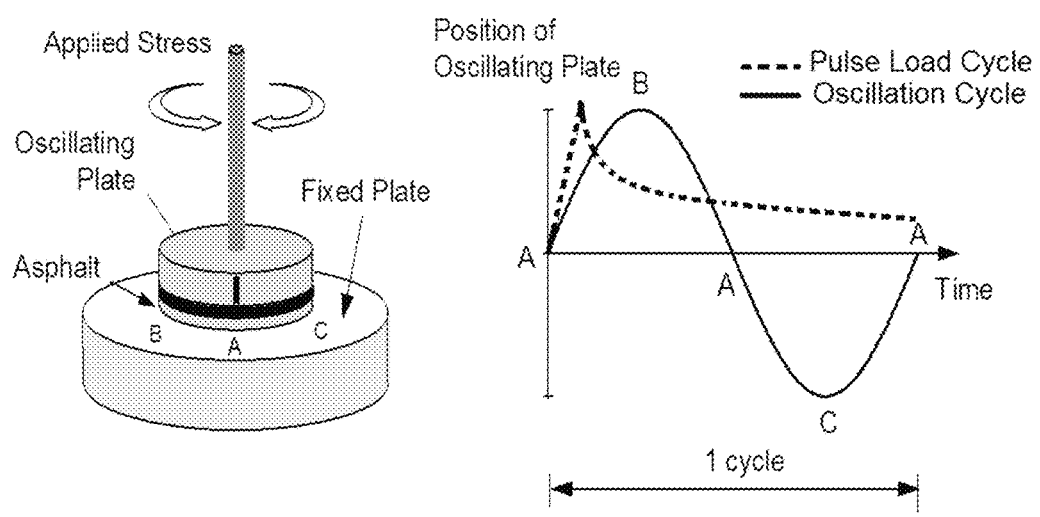
Fig. 15- Oscillating DSR versus Pulsating DSR (DSR Sinusoidal versus Pulse Load Cycle)

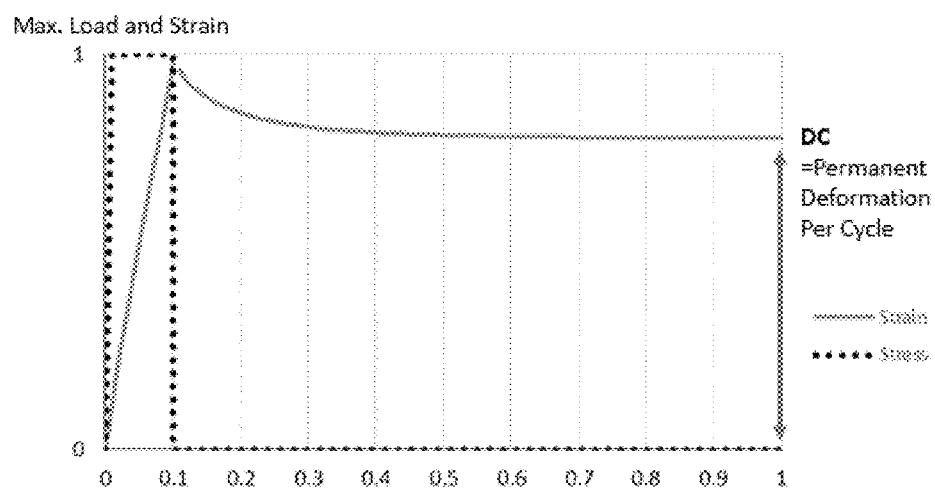
*Fig. 16- Normalized Stress and Strain of a Pulse Load Cycle and DC (Deformation per Cycle) in DSR showing the Pulse load of 0.1 s and Zero-Load of 0.9 s (rest period that heals VEM)*

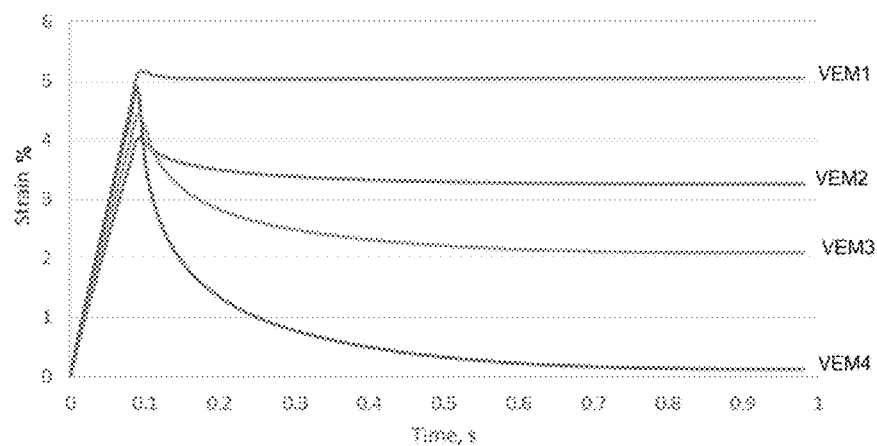
Fig. 17- A single Pulse Load Cycle for Four Different VEM tested in a DSR using the same Shear Stress and Temperature but Showing Different Response after Pulse is released

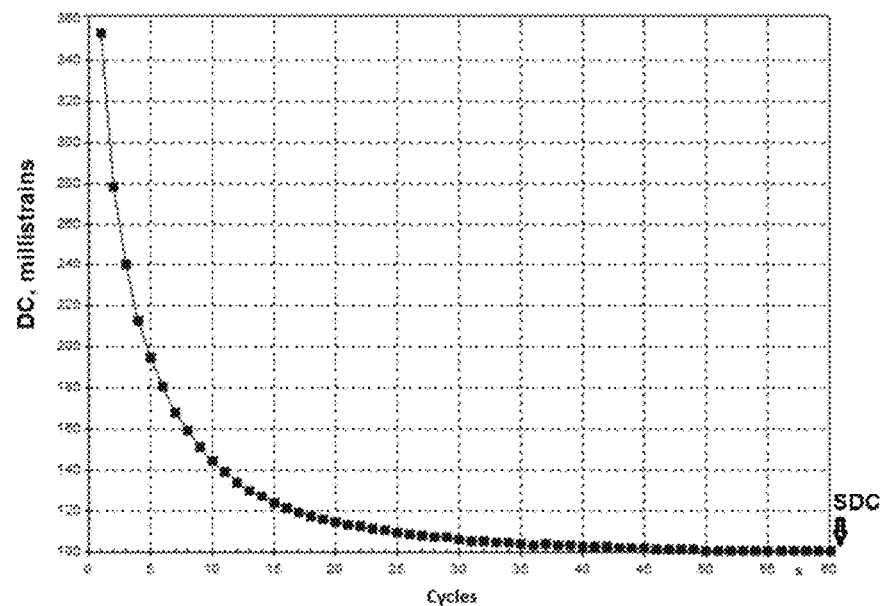
Fig. 18- DC versus Cycles for a Pulse Load Series on DSR with Sixty Cycles of 1 second

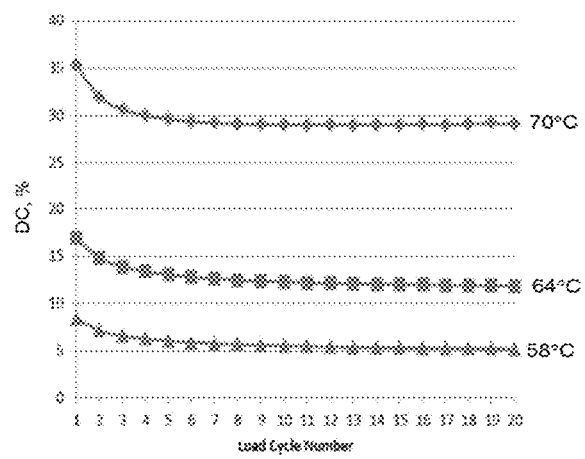
*Fig. 19- DSR Pulse Load Series for High-Temperature Test at three Temperatures*

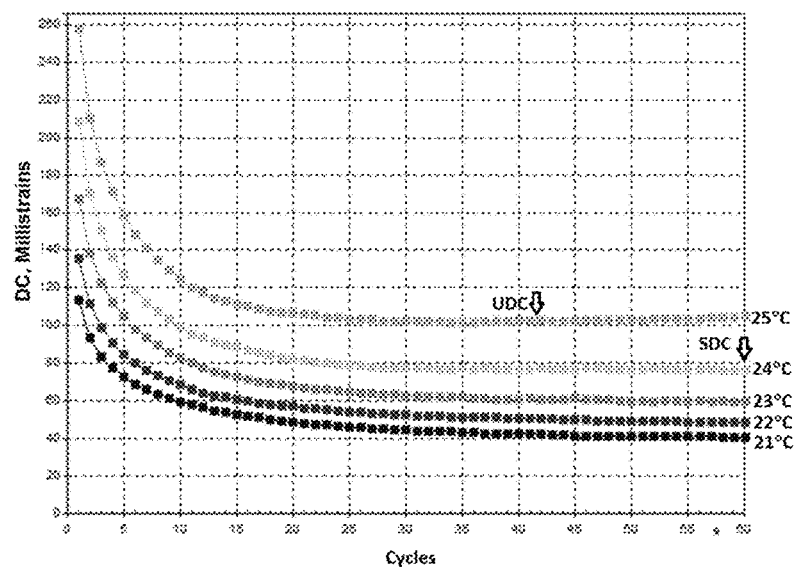
Fig. 20– DSR Pulse Load Series (PLS) for Five Temperatures in a Fatigue Test

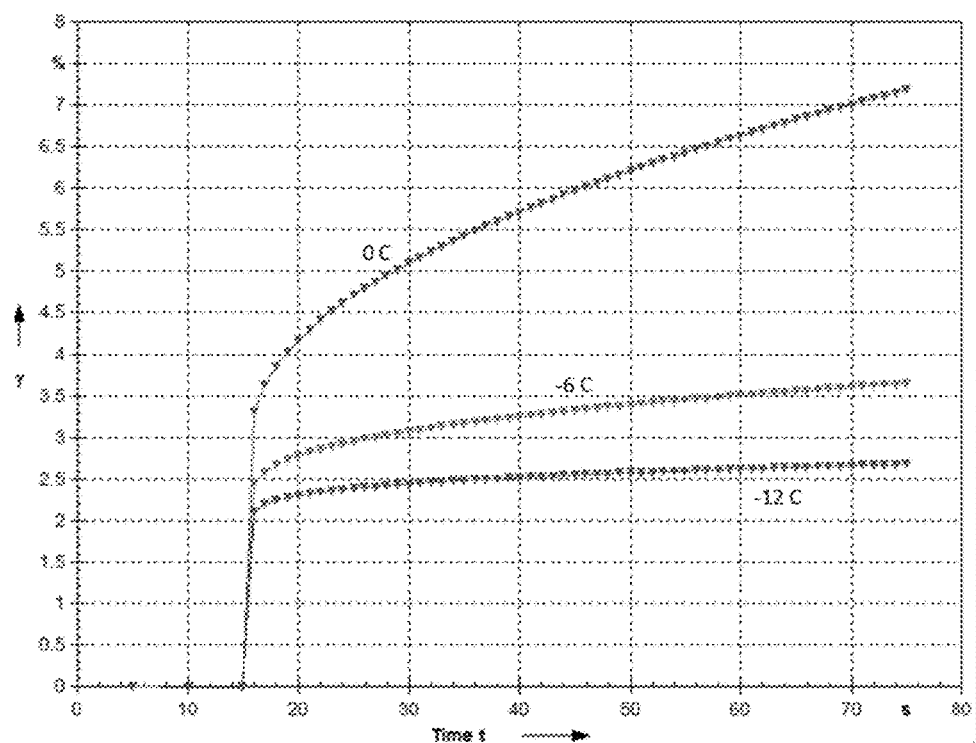
*Fig. 21- DSR Test for Low-Temperature Binder Showing Accumulated Strain for Constant Load Series at three temperatures*

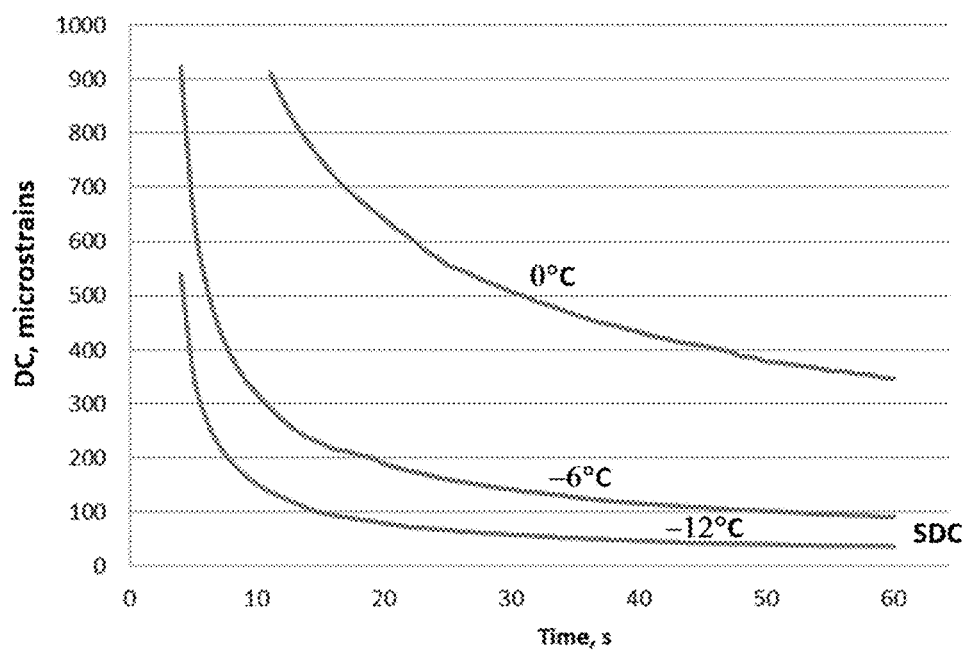
*Fig. 22- Low-Temperature Test on DSR with Constant Loading Series of sixty Cycles*

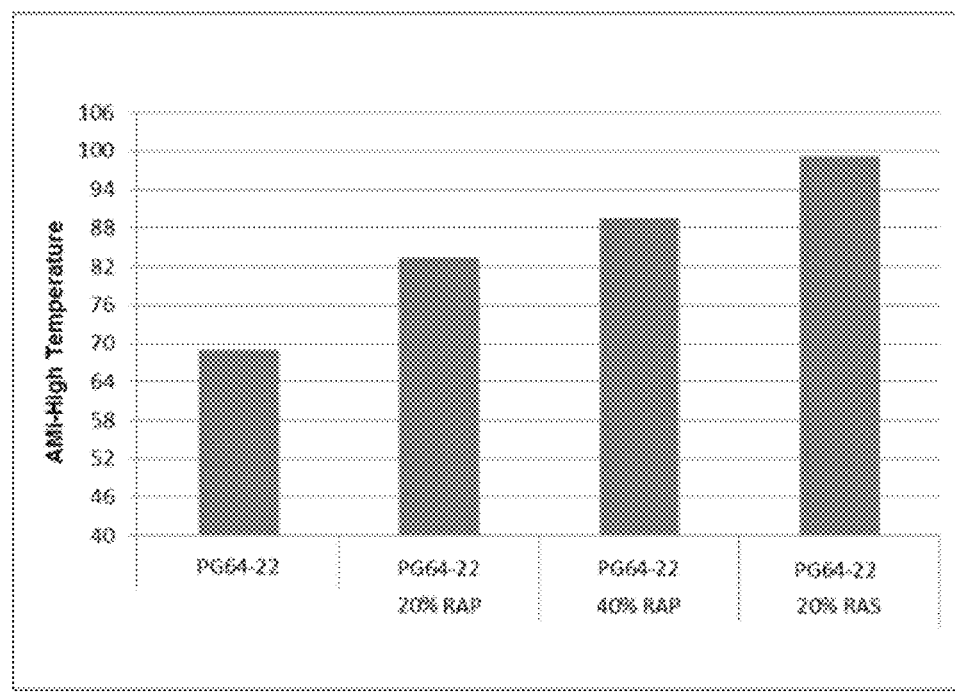
Fig. 23– Asphalt Mixture Index High-Temperature (AMI-high) for Mixture with PG64-22 binder & different Quantity of RAP and RAS

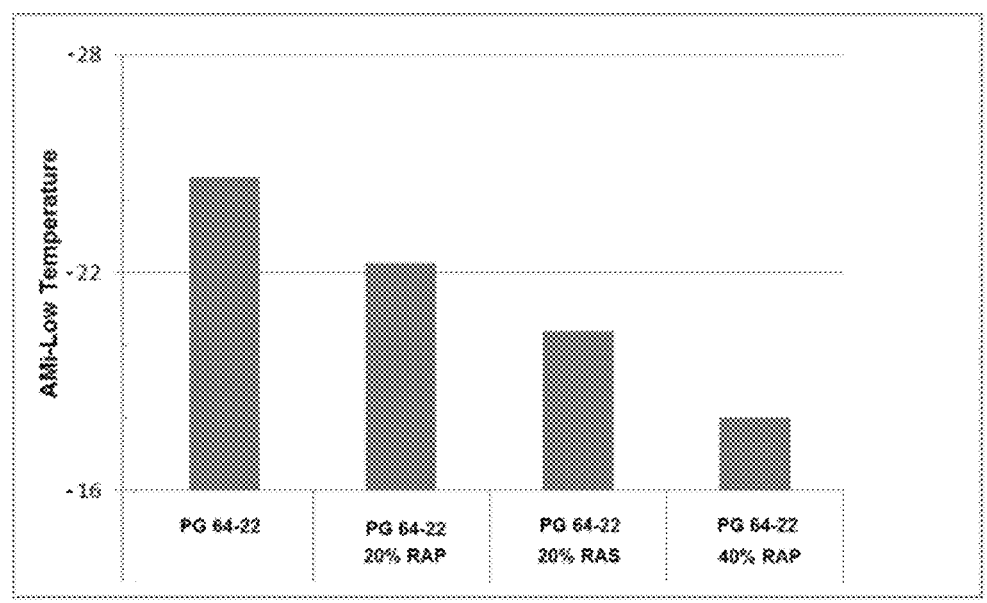
*Fig. 24- Asphalt Mixture Index Low-Temperature (AMI-low) for Mixture with PG64-22 Binder and different RAP and RAS Quantities*

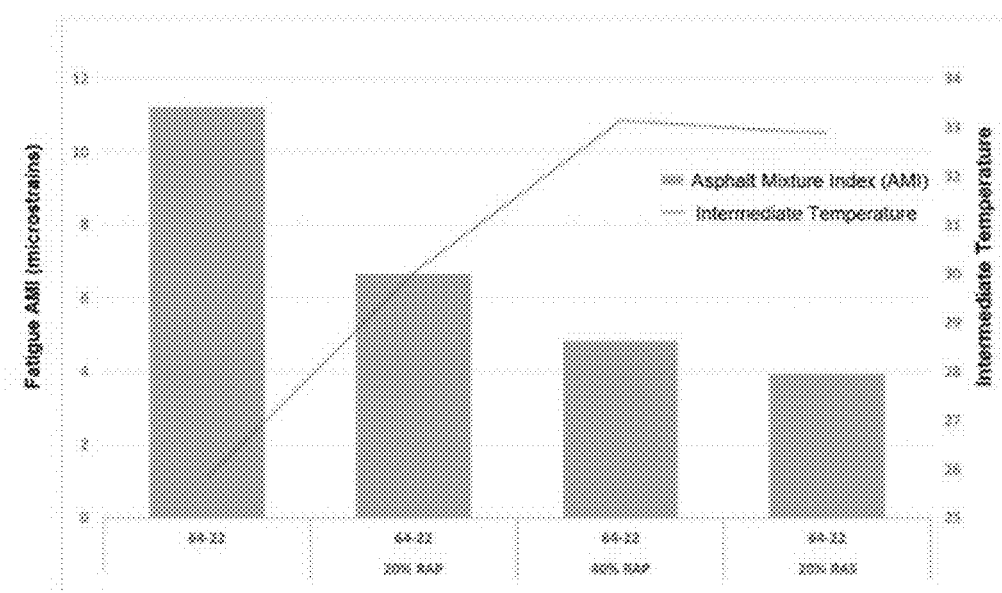
Fig. 25- AMI-fatigue for mixtures with PG64-22 binder and RAP and RAS

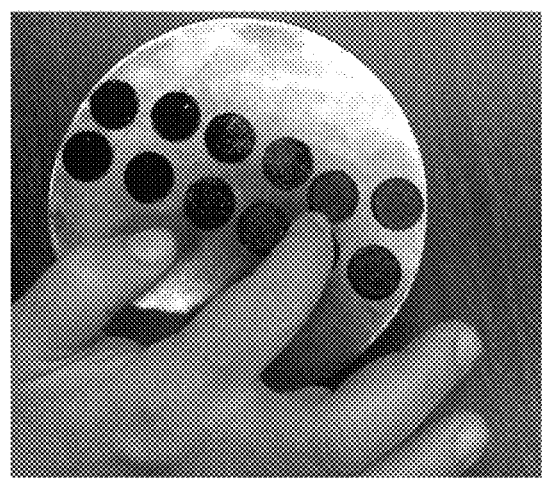
Fig. 26- Ultra-Thin Layer of Asphalt Binder Mounted on Anodized Metal Buttons for aging

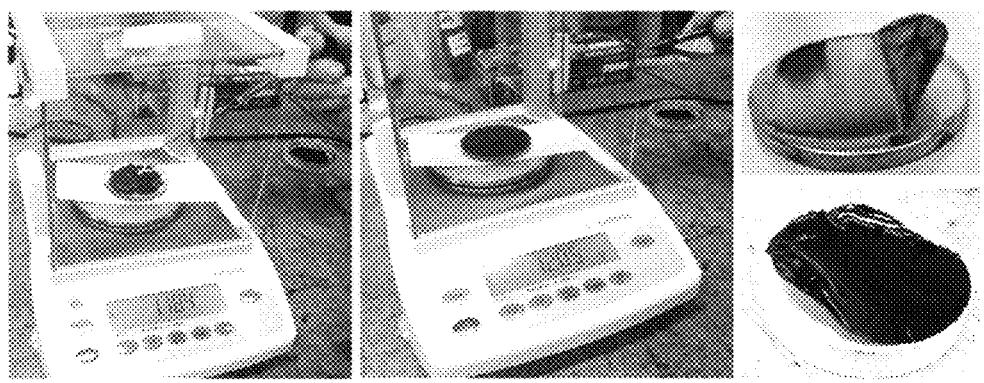
Fig. 27- Spreading Emulsions over a glass disk (Left and middle) and Recovered Asphalt Emulsions mounted on the glass or metal discs as a part of the present invention (Right)

UNIFIED PERFORMANCE TEST FOR VISCOELASTIC MATERIALS

BACKGROUND OF THE INVENTION

Field of the Invention

The present invention relates to the mechanical testing of viscoelastic materials and innovation in technologies and testing methodologies that can be utilized for determining the effect of recycled materials and various modifiers on the performance of asphalt mixtures in a unified, efficient, accurate, precise, safe, practical, and sustainable way.

Description of the Related Art

Viscoelasticity is the property of materials that exhibit both viscous and elastic characteristics when undergoing deformation. Viscoelastic materials (VEMs) show different behavior under different stress conditions. Some VEMs show different behavior under different moisture and/or temperature conditions. Capturing the effect of loading on response (i.e., deformation) of VEM is important for describing its behavior under various conditions (e.g. load level, temperature and moisture). The response of a viscoelastic material to a load or stress is usually expressed in terms of deformation or strain. The loading is performed using various loading devices.

FIG. 1 shows various Test Loading Device (TLD) used for testing VEM, including a Universal Testing Machine (UTM) in compression or tension, a Dynamic Shear Rheometer (DSR) in torsion, or Dynamic mechanical Analyzer (DMA) in compression, tension and or torsion. Usually, UTM is utilized to test large specimens, while DMA is used for medium sized specimens and DSR is used for small size specimens.

Current Standard Asphalt Binder Tests

FIG. 2 left shows a Bending Beam Rheometer (BBR) which is used for determining the low-temperature properties of asphalt binder using AASHTO T 313 standard specification. This test involves molding an approximately 10 gram bar of asphalt binder and testing it in a third point flexural device placed in the fluid bath (FIG. 2 right). A load of 100 gram is applied to the middle of the bar for the duration of 240 s and the test parameters is calculated from creep stiffness at 60 s time. The BBR test is time consuming and rather tedious to perform and suffers from several shortcomings:

1—The BBR testing device needs constant calibration
2—The liquid in bath (alcohol or anti-freeze) is a health hazard
3—The asphalt binder bar needs to be molded and de-molded which is time consuming
4—The produced bar should be tested within a narrow time limit (4 hours)
5—The bar needs over 10 gram of long-term aged material which is not easy to produce
6—Practically, only three tests may be accomplished in a full day
7—BBR should be recalibrated every time test temperature changes FIG. 3 shows the elements of a Dynamic Shear Rheometer (DSR) which consists of two plates (upper and lower plates) and a loading mechanism for one of the plates that applies a torque that causes rotation of the plate. The sample is mounted in the gap between the parallel plates. The current asphalt binder high temperature and intermediate temperature standard tests are included in AASHTO M 320, which is conducted using an oscillatory Dynamic Shear Rheometer (DSR). The DSR tests utilizes a repeated sinusoidal plate movement to determine shear stress and phase angle when material is subjected to a constant strain, which is a common method in rheology. Several studies have indicated that oscillation tests cannot determine the true asphalt performance, especially when modifiers such as polymer and rubber is used. This is because unlike the wheels loads in the field, oscillation does not allow a pause for binder to heal itself which results in premature failure.

The mounting of asphalt binder in the gap between DSR plates is performed according to AASHTO T 315 method which is based on manually trimming the outer edge of the plates by a spatula to remove the extra material (see FIG. 7). Manual trimming is tedious and leaves uneven edge which is a major cause of test variability and low precision of T 315 tests. Additionally, The T 315 mounting temperatures are not sufficient to provide proper adhesion of the binder to the plates and when high stress is used during the test, it may cause partial or full detachment of the binder from the plate. Furthermore, the AASHTO T 315 and M 320 tests are not suitable for testing VEM containing fine solid particles (filler) since manual trimming and the lack of a pause in loading prematurely damages the VEM.

Current Asphalt Aging Process

Currently, the aging of binders are conducted for two different purposes:

1—Short-term aging: to simulate aging in asphalt plant during manufacturing and storage/hauling to the construction site, and
2—Long-term aging to simulate several years of aging in service due to climatic conditions of the field.

FIG. 4 shows a Rolling Thin-Film Oven (RTFO) that performs simulated short-term aging of asphalt binder for physical and mechanical property testing. Asphalt binder is exposed to elevated temperatures to simulate manufacturing and placement aging. The RTFO also provides a quantitative measure of the volatiles lost during the aging process. The standard Rolling Thin-Film Oven test is AASHTO T 240 and ASTM D 2872: Effect of Heat and Air on a Moving Film of Asphalt (Rolling Thin-Film Oven Test). The basic RTFO procedure takes unaged asphalt binder samples in cylindrical glass bottles and places these bottles in a rotating carriage within an oven. The carriage rotates within the oven while the 325° F. (163° C.) temperature ages the samples for 85 minutes. Samples are then stored for use in physical and mechanical property tests or the Pressure Aging Vessel (PAV). RTFO oven has had several issues that limits its use, especially for polymer and recycled material.

1—A major problem for asphalt binders containing polymer and rubber is that they do not uniformly flow in the glass bottle, thus creeping out of the bottle during the process, which results in the binder not being aged properly
2—RTFO requires 35 gram in each bottle which is a lot more than needed for the new binder tests explained in this invention. The new and improved tests according to the invention only require 30 mg, which is 1000 times less
3—RTFO uses air flow that should be constantly monitored and hard to calibrate
4—The fumes of the binder can be hazardous to the lungs of the operator FIG. 5 shows a Pressure Aging Vessel (PAV) that performs provides simulated long-term aged asphalt binder for mechanical property testing. Asphalt binder is exposed to heat and pressure to simulate in-service aging over a 7 to 10 year period. The standard AV procedure is found in AASHTO R 28: Accelerated Aging of Asphalt Binder Using a Pressurized Aging Vessel (PAV). The basic PAV procedure takes RTFO aged asphalt binder samples, places them in stainless steel pans and then ages them for 20 hours in a heated vessel (usually at 100° C.) pressurized to 305 psi (2.10 MPa or 20.7 atmospheres). Samples are then stored for use in mechanical property tests. PAV oven has had several issues that limits its use, especially for polymer and rubber material.

1—In PAV steel dish the RTFO aged binder is placed in a thick layer (about 3-mm thick) and since only surface is exposed to air, the material is not oxidized uniformly 2—The pressurized air also includes nitrogen which is forced in the binder, which does not happen in the field and the binder is not oxidized similar to the field 3—PAV does not age binder to simulate the aging that occurs near the surface of pavement, which is the location where most cracks are initiated. It can only age the binder to simulate aging at the bottom of the asphalt layer.

4—Utilizing pressurized air requires safety precautions and regular safety inspections 5—PAV cannot age small quantity of viscoelastic material Asphalt Binder Extraction and Recovery The use of recycled materials in asphalt pavement can have significant economic value to the contractor and to the legislatures since it is a proper method to dispose waste. With the increasing quantity of recycled materials in asphalt mixtures, it becomes critical to understand how it interacts with virgin materials to produce a mixture that will perform successfully in service. Currently, the extraction of the recycled asphalt binder in the laboratory is a first key step in determining the properties. Following is a glossary of terms in relations to recycled asphalt materials:

Virgin Binder=Original liquid asphalt sold as binder without additives

RAP=Reclaimed Asphalt Pavement, Crushed pavements that are added to new pavements RAS=Recycled Asphalt Shingles, shingles that are pulverized for use in the new pavements GTR=Ground Rubber Tire, Tires ground to small sizes and added to new pavements REOB=Re-refined Engine Oil Bottom, engine oil that is processed for use in new pavements Asphalt Additives=Polymers, rejuvenators, anti-stripping agents, warm-mix agents, Poly Phosphoric Acid (PPA), etc.

FIG. 6 shows the equipment used for extraction of binder from asphalt mixture. Currently, the effect of recycled material (RAP, RAS, engine oil etc.) on asphalt mixture is determined by extracting the binder from the mixture using solvent extraction and testing the extracted binder. This process uses chemical solvents (e.g. trichloroethylene, trichloroethane or methylene chloride) to dissolve the asphalt binder in the mixture, to disintegrate the mixture, and then separate the liquid from the aggregate by use of a centrifuge (FIG. 6 left). The resulting liquid includes the binder and the solvent, thus solvent should be removed from the binder using a process such as Rotavapor recovery procedure (FIG. 6 right). The binder extraction and recovery process has many shortcomings:

1—It uses a complicated and time consuming (takes 2 days) process and it is expensive 2—It deals with dangerous cancer causing solutions 3—The process may leave some solvent in the binder that can affect the testing results, thus may not be the true mix representation 4—Contaminants may pass the filters and affect the property of the extracted binder 5—The extraction/recovery process may alter the molecular structure of the extracted binder, especially for the polymer and rubber modified asphalt mixtures.

For the above reasons, and particularly for the hazardous nature of the solvents, today the solvent extraction method is reluctantly used for characterization of the asphalt mixture. The current oscillatory binder test methods such as the ones in AASHTO M 320 are used for testing the binder extracted from a mixture containing recycled materials to determine the effect of recycled material; however, oscillatory method has the same limitations as mentioned earlier for testing virgin binder and cannot effectively determine the effect of recycled material.

Performance Tests for Asphalt Mixtures

Due to the increased use of recycled materials and other additives in asphalt mixtures, their performance has become rather unpredictable. This is because the virgin binder does no longer determine the performance. Therefore, testing the virgin binder does not guarantee good performance. The interaction of recycled material (RAP, RAS, REOB) with the virgin binder depends on many factors including the source of each material, their chemical and physical composition, and their level of aging (stiffening due to oxidation or loss of oil). Therefore, the only way to predict the performance of asphalt mixtures that contains the recycled material is to test the mixture itself.

Testing Asphalt mixture for performance is rather time consuming and is affected by many factors. Firstly, the hot mixture of asphalt and aggregate is compacted using an asphalt compactor. Then, the compacted samples are stored for 24 hours and then should be cut or cored to the size using a core device and a saw and only then can be tested on a loading frame such as a Universal Testing Machine (UTM). It takes days of work to prepare asphalt mixture specimens for mechanical testing and because of many factors involved, the test variability is usually rather high. FIG. 8 shows a number of asphalt mixture testing equipment that are costly to purchase, maintain and operate. This makes extensive mixture testing prohibitively expensive and impractical.

SUMMARY OF THE INVENTION

The present invention relates to a unified testing methodology for characterizing the behavior of Viscoelastic Materials (VEMs) that improves the current technology. The main invention is a new methodology for testing asphalt mixtures for determining the effect of recycled materials and modifiers. A new material called AMR and a new mounting method for Dynamic Shear Rheometer (DSR) are disclosed. A Pulsation DSR is introduced with three new test methods that provide indices for grading asphalt mixture for performance.

The first embodiment of the present invention relates to a new and innovative method of recovering the fine portion of asphalt mixture called Asphalt Mixture Residue (AMR).

The second embodiment of the present invention relates to a new method of mounting the VEM on a DSR that ensures a perfect geometry and good adhesion to the DSR plates.

The Third embodiment of the present invention relates to a new and innovative Pulse Load Series (PLS) method for a Pulsating DSR which is new to the field of rheometry. The test uses a small VEM sample such as binder or AMR to determine high-temperature properties.

The fourth embodiment of the present invention relates to the test method for fatigue properties of the VEM using the Pulsating DSR.

The fifth embodiment of the present invention relates to the low-temperature properties of the VEM using a DSR which is a significant improvement over current BBR test method.

The sixth embodiment of the present invention relates to a new and improved method of indexing the AMR. The index for AMR is develop as asphalt mixture grade comparable to the current AASHTO M320 asphalt binder Performance Grade (PG). The Asphalt Mixture Index (AMI) may be used for determining the effect of recycled materials on performance.

The seventh embodiment of the present invention relates to a new and innovative method of oxidative aging of the VEM to simulate in-use aging conditions.

The eight embodiment of the present invention relates to the normal temperature properties of the VEM under one or more PLS with high stress levels that will result in fatigue cracking of the VEM. This invention relates to all VEM under various loading devices in which load level or temperature or both are increased until VEM exhibits fatigue cracking.

The ninth embodiment of the present invention is to test the VEM in dry and saturated condition to determine the effect of moisture and moisture damage on VEM properties.

The tenth embodiment of the present invention relates to the cold temperature properties of VEM when loaded with a constant Load. This embodiment relates to testing VEM using various loading devices to determine the resistance of VEM to cracking at low temperatures. This is similar to the fifth embodiment but applies to large VEM specimens on all TLDs.

The Eleventh embodiment of the present invention relates to the hot temperature properties of VEM using one or more series of pulse loads at low stress levels. This is similar to the third embodiment but applies to large VEM specimens on all TLDs.

BRIEF DESCRIPTION OF THE DRAWINGS

FIG. 1. (Prior Art) Test Loading Devices: Universal Testing Machine—UTM (Left)—Dynamic Shear Rheometer—DSR (middle)—Dynamic Mechanical Analyzer—DMA (right).

FIG. 2—(Prior Art) Bending Beam Rheometer—BBR Device (left) and Schematic of the BBR Test Three point Bending of Asphalt Bar in Chilled Fluid (right).

FIG. 3—(Prior Art) Elements of a Parallel Plates DSR Consisting Two Plates that Create an adjustable Gap, Torque in one Plate, and Temperature Control for the Specimen.

FIG. 4—(Prior Art) Rolling Thin-Film Oven (RTFO) Equipment (left) and Bottles (right).

FIG. 5—(Prior Art) Pressure Aging Vessel (PAV) used for long-term aging of asphalt binder.

FIG. 6—(Prior Art) Open Centrifuge Used for Solvent Extraction of asphalt mixture (left), Asphalt binder recovery using a Rotavapor recovery procedure (right).

FIG. 7—(Prior Art) DSR Asphalt Mounting Method using Manual Trimming per ASASHTO 315.

FIG. 8—(Prior Art) Various Low-Temperature Asphalt Mixture Testing Equipment.

FIG. 9—Silicon Paper with Asphalt Mixture Residue According to the Present Invention.

FIG. 10—Roller for maximum particle size detection of AMR (left) AMR wrapped in paper passed through rolling mill with gap set to maximum particle size plus paper thickness.

FIG. 11—Process of Mounting Asphalt Binder or AMR on DSR According to the Invention.

FIG. 12—Melted Asphalt Binder on the DSR first plate (left), Mounted AMR with 1.0 mm Gap (middle), and mounted asphalt Binder with 0.5-mm Gap (right).

FIG. 13—Load and deformation for a Pulse Load Cycle Comprising Pulse Load and Zero Load FIG. 14—Loading Series (LS): the response (deformation) of VEM to a Series of loading cycles as applied to both Pulse Load Cycle (PLC) and Constant Load Cycle (CLC).

FIG. 15—Oscillating DSR versus Pulsating DSR (DSR Sinusoidal versus Pulse Load Cycle).

FIG. 16—Normalized Stress and Strain of a Pulse Load Cycle and DC (Deformation per Cycle) in DSR showing the Pulse load of 0.1 s and Zero-Load of 0.9 s (rest period that heals VEM).

FIG. 17—A single Pulse Load Cycle for Four Different VEM tested in a DSR using the same Shear Stress and Temperature but Showing Different Response after Pulse is released.

FIG. 18—DC versus Cycles for a Pulse Load Series on DSR with Sixty Cycles of 1 second.

FIG. 19—DSR Pulse Load Series for High-Temperature Test at three Temperatures.

FIG. 20—DSR Pulse Load Series (PLS) for Five Temperatures in a Fatigue Test.

FIG. 21—DSR Test for Low-Temperature Binder Showing Accumulated Strain for Constant Load Series at three temperatures.

FIG. 22—Low-Temperature Test on DSR with Constant Loading Series of sixty Cycles.

FIG. 23—Asphalt Mixture Index High-Temperature (AMI-high) for Mixture with PG64-22 binder & different Quantity of RAP and RAS.

FIG. 24—Asphalt Mixture Index Low-Temperature (AMI-low) for Mixture with PG64-22 Binder and different RAP and RAS Quantities.

FIG. 25—AMI-fatigue for mixtures with PG64-22 binder and RAP and RAS.

FIG. 26—Ultra-Thin Layer of Asphalt Binder Mounted on Anodized Metal Buttons for aging.

FIG. 27—Spreading Emulsions over a glass disk (Left and middle) and Recovered Asphalt Emulsions mounted on the glass or metal discs as a part of the present invention (Right).

DETAILED DESCRIPTION OF THE INVENTION

The use of recycled materials in construction can have significant economic value and environmental benefits. With the increasing quantity of recycled material used in viscoelastic materials, especially asphalt binder and mixture, understanding how they interact with original materials to produce a mixture that performs successfully becomes critical. Currently, the technology to determine the effect of additives on the performance of asphalt mixture is lacking. The present invention relates to a new unified methodology for mechanical testing of asphalt mixture and other viscoelastic materials that improves the current practice in cost, speed, convenience, lab safety, and accuracy. A new recovery method for fine portion of asphalt mixture and a new improved specimen mounting method on Dynamic Shear Rheometer (DSR) are disclosed that are essential to the grading of asphalt mixture. Subsequently, three new tests for the performance of recovered asphalt mixture using a Pulsating DSR is disclosed. The new methods provide performance grading of asphalt mixtures that is new to the industry and provide necessary tools for determining the effect of recycled materials on performance. Additionally, a new method for oxidative aging of asphalt binder and new asphalt mixture tests for fatigue, moisture damage, hot and cold condition based on the same methodology are disclosed.

New Asphalt Mixture Residue (AMR) Recovery Method According to the First Embodiment Asphalt Mixture Residue (AMR) is the fine portion of asphalt mixture having particles with a predetermined maximum diameter. The new and improved method of determining the effect of recycled material on asphalt performance in the present invention is by physically separating AMR from asphalt mixture without the use of chemical solvents which have caused numerous problems during the binder extraction/recovery process, some of which was described in the prior art. The physical separation of asphalt fine particles from the aggregate particles may be performed by various means.

FIG. 9 shows one method of recovering AMR from asphalt mixture which is by heating the mixture on a non-stick surface (e.g., surface coated with silicon or Teflon) and then manually or mechanically mixing the heated mixture. When the mixture is removed from the surface, a trace of fine particles remain, sticking to the surface. Subsequently, the surface is cooled to room temperature and shaken and or lightly rubbed so that remaining larger than predetermined diameter particles (asphalt coated particles or Ground Tire Rubber—GTR) are removed from the surface. The fine portion of asphalt mixture which is left on the non-stick surface is called Asphalt Mixture Residue (AMR). The AMR may be collected from the surface using a blade or spatula and stored in a cool place so that it is not oxidized before testing. The AMR contains material less than a predetermined size. The maximum particle diameter depends on the application. For example, for testing on DSR 8-mm parallel plate configuration with 1.0 mm gap, the maximum AMR particle size needs to be ⅓ of the gap (about 0.33 mm) so that it does not interfere with the test. For other applications where least specimen dimension is 3.0 mm, the AMR may contain particles less than 1.0 mm in size and for other applications the maximum size may differ. The non-stick surface shape may differ and mixing method and heating method may be conducted using various means.

FIG. 10 left shows a roller device that may be used to verify that AMR does not contain particles larger than a predetermined maximum size since these particles interfere with testing; for example, in a parallel plate DSR with 1.0-mm gap where the maximum particle size should not exceed 0.33-mm, or even preferably 0.25-mm. Different processes may be utilized to ensure that AMR does not contain particles larger than the maximum particle size. In one method, the AMR may be sandwiched between two non-stick surfaces and passed through a gap between two rollers set to the predetermined maximum particle size plus the thickness of the non-stick surfaces (see FIG. 10 right). Asphalt material larger than the predetermined particle size will be crushed under the roller and pulverized. The pulverized material is the indication of larger particles which may be removed from the AMR if it does not contaminate the rest of AMR or the AMR may be rejected.

The AMR recovered using the disclosed method includes the effects of recycled material (RAP, RAS, Rubber, REOB), filler, polymer, fiber, anti-stripping agents, PPA, and other additives as well as the asphalt aging (stiffening of asphalt due to oxidation during production and after construction). The AMR is subsequently tested, according to the present invention, to determine the effect of recycled material on the mixture properties, change in grade, and therefore predict performance once placed in the field.

New and Innovative DSR Specimen Mounting Method According to the Second Embodiment Proper mounting of the VEM on a DSR parallel plate is important for the conduct of the test. In the normal and low temperature DSR tests where high stress levels are utilized, lack of sufficient adhesion between the VEM specimen and the plates can cause partial or complete detachment of the VEM from one surface that will affect the test results. As discussed in prior art, current asphalt mounting method in AASHTO T 315 disturbs the sample at the edge of plates and is a major factor in test result variation (FIG. 7), the mounting temperatures of T 315 are not sufficient to provide proper adhesion to the plates, and manual trimming is not suitable for VEM with fine particles. Therefore, a new and improved VEM mounting method is disclosed in this invention for the uniform and symmetrical placement of the VEM and for achieving good adhesion between VEM and the two plates. This method is suitable for mounting virgin and aged asphalt binders and AMR, as well as any VEM that is temperature sensitive. FIG. 11 shows the proper mounting of VEM in a gap of a parallel plate DSR that should leave a reasonable bulge.

FIG. 11(1) shows the first step of mounting, according to the present invention, where sufficient VEM is weighed at room temperature such that it fills the gap and leaves a proper bulge as shown in the right side of FIG. 11. This weight is calculated from the Gap and Bulge volume and the VEM density. For example, for 8-mm parallel plate diameter (d) and 0.5 mm gap, the sufficient weight of asphalt binder aged with RTFO/PAV is between 30 to 32 mg. For the 8-mm plate diameter and 1.0 mm gap DSR geometry used for the VEM with fine particles or Asphalt Mixture Residue (AMR), 80 to 100 mg of is sufficient to fill the gap and leave a reasonable bulge. For 25-mm diameter plate and 1.0 mm Gap, about 510 mg of binder is sufficient.

FIG. 11(2) shows the second step of mounting according to the present invention where VEM is placed on the entire first plate of a DSR and the temperature is set to a first temperature and kept for a first predetermined duration to completely melt VEM. This temperature is selected such that VEM creates a symmetrical dome-shaped appearance (also see FIG. 12 right). The surface tensions always keep VEM on the surface and it will not flow over the edge. Typically, for asphalt binder and AMR, this temperature is about 30 to 50° C. higher than binder's high-temperature Performance Grade (PG); however, the temperature and the duration may vary for different VEM types.

FIG. 11(3) shows the third step of mounting the VEM, where the temperature is set to a second temperature suitable for mounting of the second plate on the asphalt dome. The second temperature is selected such that asphalt does not flow out of the gap once the plates reach predetermined gap. Typically, this temperature is 10 to 20° C. less than the first temperature for asphalt binders. Once the DSR reaches the second temperature, the second plate is moved towards the first plate to reach a predetermined gap. In the fourth step, the mounted specimen is kept under the second temperature for a second predetermined duration to achieve proper adhesion to the second plate. The second temperature and duration depends on several factors including the PG grade of the binder or AMR and whether the binder is modified using polymer, rubber, PPA, etc. The mounted specimen looks like FIG. 12 right for asphalt binder and FIG. 12 left for AMR.

Glossary of Pulse Loading Series Method for VEM According to the Present Invention New tests for the viscoelastic materials (VEM) utilize two types of loading (Constant or Pulse Loading) which may be applied using any TLD (UTM or DSR) and in any direction (compression, tension, or torsion). A segment of loading that is repeated is called a Load Cycle. For example, a 60 second constant load test may consist of 60 identical one second loading segments. Following is a glossary of terms for VEM loading methodology which is specific to the present invention. Examples and limits for each test parameter is given in the next sections when the Loading Series and new tests are disclosed for DSR and UTM.

Pulse Load Cycles (PLC) comprises a load pulse with a predetermined Maximum Stress and a predetermined duration followed by a longer zero-load (pause) period with no load. FIG. 13 top shows two pulse load cycles. Load pulse duration in this invention is typically less than 1.0 second for asphalts and is applied as quickly as possible. Zero-load does not include the constant load that is sometimes applied for keeping the sample in place (Seating Load).

Constant Load Cycle (CLC) is a special case when the VEM is subjected to a constant maximum stress for the entire cycle duration. In this method, contrary to the Pulse Load Cycle, there is no zero-load (pause) duration.

Deformation per Cycle (DC) is permanent deformation at the end of each PLC or CLC (see FIG. 13 bottom graph). DC is the deformation from the beginning to the end of one cycle and is not accumulated from previous cycles. For CLC, DC is same as max. deformation.

DC Ratio (DCR) is the ratio of DC to maximum deformation. For CLC, where DC is the same as maximum deformation, DCR is 1.0 but for Pulse Load Cycle, it is a number less than 1.0.

Loading Series (LS) is defined as a series of repeated identical Load Cycles (see FIG. 14) that when applied to a VEM, the DC is initially substantially reduced for each cycle (Initial Region) until DC becomes stable and does not significantly change (Stable Region), and finally DC reaches zero and subsequently start to increase (Unstable Region).

Pulse Load Series (PLS) is when loading cycle is Pulse Load Cycle (PLC)

Constant Load Series (CLS) is when loading cycle is Constant Load Cycle (CLC).

Deformation Acceleration (DA): The rate of change of DC, which is the change in DC at the end of any Load Cycle, compared with DC of the previous cycles (see FIG. 14). DA is a large negative number in Initial Region (DC substantially reduces with each cycle); and a small negative number approaching zero in Stable Region (DC does not change significantly); and a positive number in Unstable Region when DC starts to increase with each cycle.

Region I, Initial Region (IR) is the test region where the DC reduces significantly with each load cycle (see FIG. 14) and DA is a high negative value but reducing with each cycle.

Region II, Stable Region (SR) is the test region where the DC becomes stable (does not change significantly). DC is still reducing but at a significantly lower rate and DA is a low negative value approaching zero.

Region III, Unstable Region (UR) is the test region where DC starts to increase and DA becomes a positive value.

Stable Deformation per Cycle (SDC) is the permanent Deformation per Cycle (DC) after test enters Stable Region (SR) and before test reaches Unstable Region. Unstable DC (UDC) is the Deformation per Cycle (DC) when test enters Unstable Region (UR).

Total Deformation (TD) is the sum of all Deformations per cycles (DC) for all cycles. Span is the initial DC (for the first cycle) minus the SDC, which is the change in DC between the first cycle and the cycle when DC reaches Stable Region.

New Pulsating Dynamic Shear Rheometer (DSR)

To improve the existing VEM test methods conducted on a Dynamic Shear Rheometer (DSR), a new and innovative method called the Pulse Load Series (PLS) method is disclosed here which follows the methodology disclosed under section "Glossary of Pulse Loading Series Method for VEM" above. In the PLS method, the sample is subjected to successive Pulse Load Cycles on a DSR (Pulsating DSR). Pulsating DSR is a type of loading that would provide improved results over the currently utilized oscillatory (sinusoidal) and shear rate tests for testing the VEM on DSR (Oscillation DSR).

FIG. 15 shows the difference between a prior art Oscillation DSR and a Pulsating DSR according to the invention. It shows an oscillation cycle on DSR where the upper plate starts from position A and a torque makes it to oscillate between points B and C in a sinusoidal shape; however, in a Pulse load Cycle, the load (torque) is quickly applied that moves the upper plate from initial position A towards position B and subsequently the load is released (zero-load) and the upper plate moves back towards position A. Therefore, in oscillation, plate moves bi-directional and forces the material to move with it but in Pulse method the applied load always moves the material in one direction and then releases it to move back on itself. The Pulse Load Cycle (PLC) resembles the passing of a single wheel load over a point in asphalt pavement and for this reason, it has shown to provide much closer results to the field than oscillation. The PLC is also the preferred method for testing VEM containing fine particles (e.g. AMR) because unlike oscillation, it gives material a rest duration to heal itself and thus loading does not prematurely damages the material.

FIG. 16 shows an example of the Pulse Load Cycle (PLC) for DSR in which the VEM is subjected to a one second pulse load cycle comprising a maximum shear stress for duration of 0.1 s followed by a zero stress level (pause) for 0.9 s (stress shown by the dotted line). The solid line in FIG. 16 shows the response (i.e. strain) during the loading cycle. The strain increases to a maximum level and then when the stress is removed after 0.1 s, the VEM rebounds to some degree during the 0.9 second zero-load period. The permanent deformation at the end of 1.0 s cycle (DC) and DC Ratio (DCR) are the cycle parameters.

FIG. 17 shows examples of Load Pulse Cycles for four different VEMs (VEM1-4) tested at the same stress level. It shows that different materials rebound differently, VEM1 has the Maximum strain of 5.15% and DC of 5% with DCR of about 0.97 while VEM4 has maximum strain of 5% and DC of 0.1% and DCR of 0.02. The DC and DCR for the other two VEM are in between. This shows that some VEM can heal more than others after load is released.

FIG. 18 shows the DC versus time for Pulse Load Series (PLS) method that includes a series of identical successive Pulse Load Cycles (PLC) with stress level high enough to bring the test to the Stable Region (SR). The parameter of the PLS is Total Deformation (TD), Span and Deformation per cycle at the Stable Region (SDC) which is the cycle at which DC does not change substantially with additional cycles. FIG. 18 is an example of the Pulse Load Series (PLS) for Pulsating DSR with parallel plate configuration comprising a first and second plate. In this example, 8-mm diameter plate was used for asphalt binder with 0.5 mm gap and the test was conducted at 25° C. with 500 kPa pulse stress level. FIG. 18 shows that sixty pulse load cycles (each of 1.0 s duration) was applied to a VEM specimen and the permanent deformation per cycle (DC) has decreased from initial 350 (for the first cycle) to about 100 microstrain (for the 60th cycle) and has reached Stable Region (DC is not significantly changing with cycles). The Stable Deformation per Cycle (SDC) for this load series is then 100 microstrain and the Span is 350-100=250 microstrain. Total Deformation (TD) is sum of all DCs for all 60 cycles.

The Pulsating DSR methodology may be utilized for any VEM including but not limited to powder, soil, oil, polymers, rubber, asphalt binder, asphalt mixture, Asphalt Mixture Residue, plastics, gum, melts, and latex having any shape or size and using any DSR configuration an attachment. The test may be conducted at any temperature within the range of DSR capabilities. This includes very high temperatures (typically above 100° C.), high temperature (typically between 40 and 100° C.), normal temperature (between 0 and 40° C.), and or low temperature (typically less than 0° C.). The Pulsating DSR is ideal for testing AMR at high temperature to determine asphalt rutting potential and at normal temperature to determine its fatigue resistance and to grade asphalt mixture.

Improved High-Temperature Test Using PLS Method According to the Third Embodiment The present invention discloses a new and innovative methodology for testing VEM at high-temperature using a Pulsating Dynamic Shear Rheometer (DSR). The invention comprises mounting the VEM specimen on a DSR, setting the temperature to a predetermined hot temperature and allowing sufficient time for the uniform spread of temperature, and applying a Pulse Load Series (PLS) of a first predetermined stress until the test reaches the Stable Region (SR) and does not reach Unstable Region (UR).

FIG. 19 shows an example of high temperature test using PLS method on DSR for a PG70-22 binder at three temperatures where the SDC at 70° C. is around 29%. In this example, the pulse stress level was 5.0 kPa for duration of 0.1 s and Stable Region was reached after 20 cycles of one second each. Optionally, the stress may be increased to a second and third predetermined levels and the PLS be repeated at each level stress level to provide an SDC corresponding to each stress level.

In another embodiment of the present invention, the test is conducted on a DSR with parallel plates of 8-mm diameter and the gap depth of 0.5-mm for asphalt binder or 1.0-mm for AMR or VEM with fine particles. For oxidized asphalt binder using RTFO procedure, the binder is mounted on DSR, the temperature is set to high-temperature PG (Performance Grade) of the binder and PLS with maximum stress of typically between 1 and 30 kPa is applied for 60 cycles. The maximum stress level varies with the DSR geometry and VEM type, however, it should be high enough to bring VEM to the Stable Region (SR) but not excessively high to cause the test to enter the Unstable Region. In the high-temperature test, the PLS should always end in the Stable Region (SR) where DA is a low negative number close to zero.

In another embodiment of the present invention, the Pulsating DSR with parallel plates of 25-mm diameter is used for a very-high temperature test. The gap between parallel plates is 1.0-mm and the temperature is set to a very high temperature between 100 and 200° C. that melts VEM. Once the VEM is mounted on a DSR, the temperature is set to a predetermined temperature and sufficient time is allowed for uniform thermal condition, a PLS is applied on the VEM with 0.1 s load and 0.9 s zero-load period. In this embodiment, since VEM is in the fluid state, the test is always past initial and stable region and will be in the Unstable Region (UR) and DC is higher than the maximum strain. The test stress level is selected based on the type of DSR geometry and VEM type such that DC is not so excessive to force the VEM outside the mounting. The test parameters are Span, Total Deformation (TD) and Stable Deformation per Cycle (SDC) and the end of each Load Series. One variation of this test is for virgin asphalt binder tested at the mixing or compaction temperature.

The high-temperature DSR test may be conducted on a variety of VEM materials including but not limited to oil, recycled engine oil (REOB), rubber, rubber improved materials, gum, polymer, latex, plastic, original asphalt binder, oxidized asphalt binder, asphalt emulsions, recovered AMR or asphalt binder from asphalt mixture. The temperature may be any high temperature typically above 30 and mostly between 40 and 100° C.

Improved Fatigue Test for Pulsating DSR According to the Fourth Embodiment

The present invention discloses a new and innovative VEM fatigue test method using a Pulsating Dynamic Shear Rheometer (DSR). The invention comprises mounting the VEM specimen on a DSR, setting the temperature to a first predetermined normal-temperature between 0 and 40° C. and applying a Pulse Load Series (PLS) until test reaches the Stable Region (SR) and does not reach Unstable Region (UR) in the first PLS. The test parameters are TD, Span and the Stable Deformation per Cycle (SDC) at the end of each PLS. The stress magnitude is selected based on DSR geometry and VEM type such that it can bring the material to the Stable region and induce measurable amount of SDC.

FIG. 20 shows an example of fatigue test output for an asphalt binder. The test is conducted on a DSR with parallel plates of 8-mm diameter and the gap depth of 0.5-mm. The lowest curve in FIG. 20 discloses the first Pulse Load Series (PLS) consists of 60 cycles of one seconds each (500 kPa stress and 0.1 s load pulse duration), applied to VEM after it has uniformly reached 21° C. The Deformation Acceleration (DA) at the end of first PLS is still negative (DC is reducing), which is an indication that the material is still in the Stable Region and has not reached Unstable region. The SDC at this temperature is about 40 millistrains. The temperature is subsequently raised by one degree to 22° C. and the same PLS is repeated (second line from bottom) and the DA is still negative. The PLS is repeated at 23° C. and 24° C. and the DA is approaching zero at 24° C. Repeating the PLS at 25° C. causes the DA to become negative (DC starts to increase) which is the indicative that material has entered Unstable Region (UR). At this PLS, the VEM has initiated fatigue cracking. The cycle when VEM enters Unstable Region (marked as UDC in FIG. 20) is the cycle that fatigue cracking is initiated. The fatigue index of VEM, according to the present invention, is the SDC in the PLS before the material reaches Unstable Region and DA is zero. Fatigue index indicates how much the material may be strained in a Pulse Load Series before it starts to exhibit cracking. The temperature for the PLS before the material initiates cracking (SDC) is called Intermediate Temperature (IT) of the material. Therefore, the material in FIG. 20 has Fatigue Index (SDC) of about 80 millistrain at the Intermediate Temperature of 24° C.

In one embodiment of the present invention, the test is conducted on a DSR with parallel plates of 8-mm diameter and the gap depth 1.0-mm for AMR or VEM with fine particles. For oxidized asphalt binder using RTFO plus PAV procedure, the VEM is mounted on DSR, the temperature is set to normal temperature and PLS with maximum stress of typically between 400 and 800 kPa is applied. The stress should be such that a series of 60 cycles is adequate to bring the test to the Stable Region (SR). This test may be conducted on a variety of VEM materials including but not limited to oil, recycled engine oil (REOB), rubber, rubber improved materials, gum, polymer, latex, plastic, original asphalt binder, oxidized asphalt binder, asphalt emulsions residue, recovered AMR. The initial temperature and maximum stress for PLS is determined such that VEM reaches the Stable Region (SR) but does not reach the Unstable Region in the first load series. However, the VEM should reach the Unstable Region (UR) by applying four to eight PLS at different temperatures in order to reach intermediate temperature.

New and Improved Low-Temperature Test for DSR According to the Fifth Embodiment

The present invention includes a new and innovative Low-Temperature test method for VEM using a Dynamic Shear Rheometer (DSR). As mentioned before, the current standard for low-temperature test is conducted using BBR which has significant limitations. However, the present invention has removed several of the limitations of the BBR by utilizing a DSR while providing comparable asphalt Performance Grade (PG).

The invention comprises mounting the VEM specimen on the DSR, reducing the temperature to a first predetermined Low Temperature typically equal to or less than 0° C. and waiting for uniform temperature reached, and subsequently applying a constant predetermined shear stress (CLS) such that test reaches the Stable Region (SR) and does not reach Unstable Region (UR). The specimen temperature may be reduced to a second or third or fourth predetermined test temperature and the test repeated. The test parameters are Span, Total Deformation (TD) and Stable Deformation per Cycle (SDC) and the end of each Load Series. The test stress level is selected based on the type of DSR geometry and VEM type such that it can bring the VEM to SR and the SDC can be a measurable amount.

FIG. 21 shows an example of the test conducted on a DSR with parallel plates of 8-mm diameter and the gap depth of 0.5-mm utilizing 1000 kPa stress for an asphalt binder that is oxidized using RTFO/PAV procedures. The y-axis (Y) is the total strain in % and x-axis is time in seconds. The test was conducted in three steps. In the first step, the temperature is reduced to 0° C. and sufficient time is allowed for the VEM to uniformly reach the temperature. Subsequently, a CLS (Constant Load Series) of 60 cycles (each one second duration) applied to bring the test to the Stable Region. In the next step, the VEM temperature is reduced to −6° C. and the same CLS repeated. This process is repeated after reducing the temperature to −12° C. where TD (total strain) at the end of cycle was 2.7%.

FIG. 22 shows similar data to FIG. 21 in terms of Deformation per Cycle (DC) for Constant Load Cycle (CLC) of one second cycle time. The line for −12° C. shows that DC was initially about 540 microstrains (ms) but reduced substantially in Initial Region and reached the Stable Region (SR) after 60 cycles (seconds). This is evidenced by negative DA which indicates that DC is still reducing at the end of 60 s. The Stable Deformation per Cycle (SDC) for this Load Series is about 30 microstrain (ms).

In one embodiment of the present invention, the test is conducted for AMR or VEM with fine particles with 8-mm plate diameter and the gap depth of 1.0-mm. For oxidized asphalt binder using RTFO plus PAV procedure, the VEM is mounted on DSR, the temperature is set to Low temperature and CLS with maximum stress of typically between 100 and 1500 kPa is applied. The stress should be such that it brings the test to the Stable Region (SR) but does not reach Unstable Region. This test may be conducted on a variety of VEM materials including but not limited to oil, recycled engine oil (REOB), rubber, rubber improved materials, gum, polymer, latex, plastic, asphalt binder, oxidized asphalt binder, recovered AMR. The temperature may be any low temperature less than equal 0° C., but normally the temperature can be set to a fix predetermined temperature (e.g. −5° C.) or like BBR test, 10° C. above the low-temperature PG of the asphalt binder (−6, −12, −18, −24 or −30° C.).

New and Innovative Asphalt Mixture Index (AMI) According to the Sixth Embodiment Currently, a grading for asphalt mixture does not exist. The grading of asphalt mixture is critical for determining the effect of recycled material on asphalt performance. The new and innovative Asphalt Mixture Residue (AMR), the new mounting method for DSR, and Pulsating DSR disclosed as a part of the present invention is utilized to disclose a new grading system for the Asphalt Mixture called Asphalt Mixture Index (AMI). The AMI is determined by testing AMR utilizing high and low temperature and fatigue cracking tests on DSR separately or consecutively in a series of tests with a single mounting. Therefore, new grading system comprises three components for AMI-high, AMI-low, and AMI-fatigue. In all three DSR test methods, TD, Span and Deformation per Cycle at Stable Region (SDC) parameter is used for grading the mixture similar to the grading of asphalt binder. When only virgin binder without additives is used in the mixture, AMI grade will be similar to binder PG; however, with the addition of recycled material (RAP and RAS) AMI changes.

FIG. 23 discloses an example of High-Temperature grade (AMI-high) for four asphalt mixtures that have same binder grade (PG64-22) but different quantity of RAP and RAS. The AMR was recovered from the asphalt mixture and was tested using at the High-Temperature using Pulsating DSR to determine the SDC. AMI-high is the temperature at which SDC has a predetermined value. FIG. 23 discloses that the AMI substantially increases (from 68 to 84° C.) when 20% RAP is added to the mixture. This is due to the stiffening of the mixture as a result of using RAP, which is much stiffer old pavement that are crushed and added to new pavements. The addition of 20% RAS (Shingles) increases the AMI to 99° C.

FIG. 24 discloses the Low-Temperature Asphalt Mixture Index (AMI-low) determined using the mixture AMR and the CLS method of DSR. The AMI-low is the temperature at which SDC is a predetermined value. FIG. 24 shows AMI-low for the same mixtures as for AMI-high. The AMI was reduced from −24.5° C. for PG 64-22 mixture to about −22° C. when 20% RAP and −18° C. when 40% RAP was used in the mixture. The increase in AMI-low is caused by the effect of recycled material which significantly reduces the asphalt durability.

FIG. 25 discloses the Mixture Fatigue Cracking Index AMI (AMI-fatigue). The AMI-fatigue is the SDC of the Pulsating DSR fatigue test at intermediate temperature. FIG. 25 shows AMI-fatigue for the same mixtures as for AMI-high. The AMI is 11.0 microstrains (ms) for mixtures without RAP or RAS but reduces to 6.5 ms for mixture with 20% RAP and further to 5 ms for mixture with 40% RAP. For mixture with 20% RAS (Shingles), the AMI further drops to 4 ms which shows that the mixture has lost its fatigue resistance due to the use of RAP.

The three AMIs disclosed in the present invention can be quickly determined and the Pulsating DSR tests are easy to perform. It does not suffer from numerous limitations and shortcomings of extracting binder from mixture and current standard asphalt binder tests. The AMR recovery process may be performed in the laboratory, asphalt plant or at the time of construction within a few minutes. The recovered AMR may be immediately tested to determine the AMI and asphalt mixture performance grade in less than 30 minutes. The cost of performing the AMI tests is a fraction of the cost of performing mixture tests and is much safer. For this reason, the AMI tests are ideal for Quality Control of asphalt mixtures.

Ultra-Thin Film Aging of Asphalt Binders and AMRs According to the Seventh Embodiment FIG. 26 discloses a new and innovative aging procedure in the present invention that resolves numerous issues with the current asphalt aging process using RTFO and PAV. The new and innovative method utilizes very thin layers of VEM (asphalt binder or AMR) on flat surfaces. VEM is placed on a flat surface in an ultra-thin film thickness similar to steps 1 and 2 of DSR mounting method by weighing and melting VEM. The thickness is approximately 250 microns for asphalt binders (12 times less than PAV) and typically between 200 and 600 microns for all applications. The ultra-thin layer makes oxidation significantly easier and more homogeneous in a regular force draft oven without the need to pressurize the oven. The material is then evenly mounted on the surface of a metal or glass disk (FIG. 26). The material is subsequently transferred to a forced-draft oven for aging. Typical aging times and temperatures for asphalt binders and AMR are as follows:

1—Short-term aging of asphalt binder is performed in 60 minutes duration at about 120° C. to simulate RTFO or between 100 to 200° C. for other applications
2—Long-term aging of asphalt binder (PAV) may be performed for 20 hours at 100° C.
3—Long-term aging of Asphalt Mixture Residue (AMR) may be performed at 85° C. for various length of time to simulate aging at different time.

Oxidative aging of any VEM including oil, rubber and rubber improved materials, polymer and polymer modified material, gum, and paint may be conducted using this method but at proper temperature and duration.

Ultra-Thin Film Recovery and Aging of Asphalt Emulsions

FIG. 27 discloses a variation of the present invention for the residue recovery and oxidative aging of asphalt emulsions on flat surfaces that improves the current process. The recovered and aged emulsions may be tested with DSR for hot, normal and cold temperature properties.

The first step is the mounting of emulsions on the flat surface that is shown in the FIG. 27 left and middle where a predetermined weight of emulsions is evenly spread over the surface to create a predetermined layer thickness. The weight is determined from the layer thickness and the emulsions density (which is normally close to 1.0). For example, applying 1.2 gram of emulsions over a 2.5 in. diameter glass disk, will create a 0.38 mm layer. This thickness is similar to the current AASHTO PP72 Method B specification; however, this method may be applied to any other layer thickness and VEM including heated asphalt binder and AMR. Some of the applications of the present mounting is as follows:

1—To recover the emulsions, the disc is placed in forced-draft oven at 60° C. for 6 hours.
2—Alternatively, the emulsions may be recovered in a heated vacuum chamber with the temperature of 60° C. and absolute pressure of 5-mm HG for shorter time period, or any other combination of temperature, vacuum level, and duration.
3—For long-term aging, the recovered binder resulting from 1 or 2 above may be aged in the forced-draft oven for 16 hours at 125° C., or any other combination of temperature and time depending on the application.

Unified Test Methods for Fatigue of VEM, Moisture Susceptibility, Hot and Cold Condition FIG. 13 and FIG. 14 describes the basis for Constant and Pulse Load Series (CLS and PLS) methods for testing VEM. Four unified test methods are disclosed here based on the Load Series methodology in the current invention. These test methods cover three different temperature ranges and a moisture state using any Test Loading Device (TLD) as follows:

1. Hot Condition test conducted at temperatures over 30° C. The hot condition test determines the VEM behavior when subjected to a Pulse Loads Series with low level stress and at elevated temperatures.
2. Normal Condition test conducted between 0 and 40° C. The normal temperature test relates to the fatigue cracking behavior of VEM when subjected to a Pulse Loads Series at high stress levels and at normal temperatures. Moisture Condition test is a variation of normal condition test that is conducted at a single room temperature (about 25° C.) on moisture conditioned specimens to determine the effect of moisture on VEM.
3. Cold Condition test conducted at temperatures below 0° C. The cold temperature test determines the cracking resistance of VEM at cold temperatures.

Test Procedure for Normal Condition Test According to the Eight Embodiment

1. VEM is placed under a Loading Device (TLD) at a normal temperature condition (between 0 and 40° C.) and a Load Series (PLS or CLC) with high stress level is applied to the material until DC reaches the Stable Region (SR) but does not reach the Unstable Region (UR). The Total Deformation (TD), Span and Deformation per Cycle at Stable Region (SDC) is the test parameters. The applied load magnitude should be high enough to induce a measurable amount of SDC but not too high to reach UR.
2. Optionally, the load may be increased to a higher level and step 1 above repeated on the same VEM sample. This process may be repeated several times for several load levels and each load level will produce an SDC.
3. The same VEM is set to a higher temperature and the test as in 1 (and optionally 2) is then repeated on the same VEM which results in new SDC for the higher temperature.
4. The process in 1 to 3 above is repeated until test reaches Unstable Region where Deformation Acceleration (DA) becomes positive and DC starts to increase per additional cycle. The TD, Span and SDC for the PLS before test reached UR is defined as test parameters.

Test Procedure for Moisture Condition Test According to the Ninth Embodiment

1. VEM is placed under a Test Loading Device (TLD) at a dry condition and a Loading Series (CLS or PLS) is applied to the material until test reaches the Stable Region but does not reach Unstable region (UR). Optionally, the load may be increased to a higher level and the test repeated on the same VEM. This process may be repeated several times for several load levels until SDC reaches a predetermined value. (give example of the value) The Deformation per Cycle at Stable Region (SDC) is then defined as the initial SDC. (numerical example of how calculated and used)
2. VEM is saturated with moisture to a predetermined level and another Loading Series is applied on the same specimen at the highest stress level in item 1 above. Optionally, the specimen may be frozen for any length of time and subsequently thawed before or after loading. This process may be repeated several times.
3. The VEM is then dried (moisture is removed from sample) to a predetermined level and another Loading Series is applied on the same sample at the same stress level as in item 2 above and the Final SDC is noted.
4. Test parameter is the ratio of Initial SDC to Final SDC which shows the degree VEM has lost integrity due to moisture. (give example of ratio)

According to one embodiment of the present invention, the test is conducted as a variation of the normal condition test described before. The PLS in steps 1 and 2 of the second embodiment are performed on the specimen at a single room temperature until a measurable amount of SDC is reached and the load magnitude is noted. The same VEM specimen is subsequently fully saturated with water under high vacuum and the last PLS and load level is repeated on saturated specimen. Subsequently, the water is removed from VEM specimen and it is dried to a predetermined level and the last PLS is repeated again.

Test Procedure for HOT Condition Test According to the Tenth Embodiment

The hot condition test utilizes a loading Series (PLS or CLS) similar to the Normal Condition described above with the exception that the test is conducted at high temperature (above 30° C.) and lower load (or stress) level according to the type of application. The load level is selected based on Pulse Load Cycle (PLC) such that the test reaches the Stable Region (SR) and does not reach the Unstable Region (UR) and the SDC is a measurable amount (i.e. step 4 of the normal condition is ignored). This means that the Deformation Acceleration (DA) should always be negative and DC should always be reducing per cycle. (Give numerical examples of DA and its calculation and use.)

Test Procedure for COLD Condition Test According to the Eleventh Embodiment

1. VEM is placed under a Test Loading Device (TLD) at a cold condition (less than 0° C.) and a Load Series (CLS or PLS) with high stress level is applied to the material until test reaches the Stable Region (SR) and does not reach the Unstable Region (UR). The Total Deformation (TD), Span and Deformation per Cycle at Stable Region (SDC) is then defined as the test parameters. (give numerical examples for calculating test parameter and how they are used in the test) The applied load magnitude should be high enough to induce a measurable amount of SDC but not too high to reach UR.
2. Optionally, the load may subsequently be increased to a higher level at the same temperature and the CLS be repeated on the same VEM as in 1 above. This process may be repeated several times for several load levels and each Load Series will have an SDC.
3. Optionally, the temperature of the same VEM may be set to another temperature and the test is repeated which results in a new set of SDC for the new temperature.
4. The process in 1 to 3 may be repeated as many times as needed.

The cold, normal, moisture, and hot condition tests may be utilized for any VEM including powder, polymers, rubber, asphalt binder, asphalt mixture, asphalt mixture residue, plastics, gum, and latex having any shape or size and using any type of Test Loading Devices (TLD).

The invention claimed is:

1. A unified test method of mechanical properties of viscoelastic materials (VEM) using a Dynamic Shear Rheometer (DSR) having a first and a second parallel plate configuration comprising:
   placing the VEM between the first and second plates;
   performing a high-temperature test by setting the temperature to a predetermined high-temperature above 40° C. and applying one or more first Pulse Loads Series (PLS) sufficient to cause deformation in the VEM, wherein the VEM reaches a first Stable Region wherein a first DA is a negative number that approaches zero and does not reach a first unstable region wherein the first DA becomes positive, and/or
   performing a low-temperature test by setting the temperature to a predetermined low-temperature equal or less than 0° C. and applying one or more Constant Load Series (CLS) sufficient to cause deformation in the VEM, wherein the VEM reaches a second Stable Region and does not reach a second Unstable Region, and/or
   performing an intermediate temperature test by setting an intermediate temperature between 0 and 40° C. and applying a second Pulse Load Series at a predetermined maximum stress sufficient to cause deformation in the VEM, wherein the VEM reaches a third Stable Region and does not reach a third Unstable Region, and further applying different iterations of Pulse Load Series with the same predetermined maximum stress as the second Pulse Load Series and at higher temperatures than was applied during the second Pulse Load Series until the VEM reaches a subsequent Unstable Region.

2. The method of claim 1, wherein the VEM is one or more of an oil, powder, melts, paint, polymer, gum, polymer modified material, rubber, rubber products, original asphalt binder, aged asphalt binder, extracted asphalt binder from mixture, and/or Asphalt Mixture Residue.

3. The method of claim 1, wherein a diameter of each of the first and second plates is 8 mm,
   wherein if an asphalt binder is used for the VEM, a gap between the parallel first and second plates is 0.5 mm, and
   wherein if an Asphalt Mixture Residue is used for the VEM, the gap between the parallel first and second plates is 1.0 mm.

4. The method of claim 3, wherein the VEM is the asphalt binder and further comprising, during the high, low, and/or intermediate temperature tests, determining a temperature at which a predetermined deformation per cycle at Stable Region (SDC) occurs which is a binder Performance Grade (PG) for the asphalt binder.

5. The method of claim 3, wherein the VEM is the Asphalt Mixture Residue (AMR) and further comprising, during the high, low, and/or intermediate temperatures tests, determining a temperature at which a predetermined deformation per cycle at Stable Region (SDC) occurs which is an Asphalt Mixture Index (AMI) for an asphalt mixture from which the Asphalt Mixture Residue (AMR) is obtained.

6. The method of claim 5, wherein the AMI is a grade of the asphalt mixture from which the AMR is obtained at low, high and intermediate temperatures and determines the effect of recycled material on an original binder.

7. The method of claim 1, wherein the placing of the VEM between the first and second plates comprises:
a method of mounting the VEM on a gap between the first plate and the second plate of the Dynamic Shear Rheometer (DSR) comprising:
  a. weighting an appropriate amount of the VEM to fill the gap of a predetermined thickness and create a bulge,
  b. placing the VEM on the first plate surface,
  c. heating the VEM to a first temperature until it melts and spreads so as to substantially cover the entire first plate surface creating a symmetrical dome-shaped appearance,
  d. reducing the temperature to a second temperature suitable for adhesion of the VEM to the second plate;
  e. moving the first plate and the second plate towards each other to the predetermined gap, and
  f. allowing sufficient time for the VEM to adhere to the second plate.

8. The method of claim 7, wherein the VEM is one or more of an oil, powder, melts, paint, polymer, polymer modified material, rubber, rubber products, original asphalt binder, aged asphalt binder, extracted asphalt binder from mixture, and/or Asphalt Mixture Residue.

9. The method of claim 7, wherein a diameter of each of the first and second plates is 8 mm,
wherein if an asphalt binder is used for the VEM, the gap between the parallel first and second plates is 0.5 mm, and
wherein if an Asphalt Mixture Residue is used for the VEM, the gap between the parallel first and second plates is 1.0 mm.

10. The method of claim 7, wherein a diameter of each of the first and second plates is 25 mm, and wherein if an asphalt binder is used for the VEM, the gap between the parallel first and second plates is 1.0 mm.

11. The method of claim 1, wherein the VEM is an Asphalt Mixture Residue (AMR) and further comprising obtaining the AMR by a method of recovering the Asphalt Mixture Residue (AMR) from an asphalt mixture, comprising:
  a. Heating the asphalt mixture to a mixing temperature until it becomes soft,
  b. Evenly spreading the heated asphalt mixture over a non-absorbing surface,
  c. Continue heating and Periodically mixing and spreading the asphalt mixture until a fine residue is attached on the non-absorbing surface,
  d. Discarding the asphalt mixture from the non-absorbing surface,
  e. Shaving off sands and stones from the non-absorbing surface,
  f. Collecting the AMR.

12. The method of claim 11, wherein the fine portion of asphalt mixture has a particle size that is less than 0.25 mm in diameter.

13. The method of claim 11, wherein the fine portion of asphalt mixture has a particle size that is less than 0.33 mm in diameter.

14. The method of claim 11, wherein the fine portion of asphalt mixture has a particle size that is less than 0.50 mm in diameter.

15. The method of claim 11, wherein the fine portion of asphalt mixture has a particle size that is less than 1.0 mm in diameter.

16. The method of claim 11, wherein the non-absorbing surface is flat, or curved.

17. The method of claim 11, wherein the mixing is either of manual or mechanical.

* * * * *